United States Patent [19]

Putsche, Jr.

[11] Patent Number: 5,252,541

[45] Date of Patent: Oct. 12, 1993

[54] MARIJUANA ERADICATION USING FLUORESCEIN DYES

[76] Inventor: Fred W. Putsche, Jr., 517 La Claire Ave., Linthicum, Md. 21090

[21] Appl. No.: 820,764

[22] Filed: Jan. 15, 1992

[51] Int. Cl.$^5$ .............................................. A01N 43/16
[52] U.S. Cl. .................................................. 504/297
[58] Field of Search .................. 71/88; 549/223, 224; 504/297

[56] References Cited

U.S. PATENT DOCUMENTS

| | | | |
|---|---|---|---|
| 2,222,225 | 11/1940 | Green | 71/88 |
| 4,500,343 | 2/1985 | Burow, Jr. | 71/76 |
| 4,781,843 | 11/1988 | Baker et al. | 71/67 |

*Primary Examiner*—Richard L. Raymond
*Assistant Examiner*—S. Mark Clardy
*Attorney, Agent, or Firm*—Robert M. Downey

[57] ABSTRACT

A method of eradicating unwanted vegetation, such as the marijuana plant, the method including the steps of preparing a predetermined concentration of fluorescein or like dye, the dye including a photodynamic pigment which in the presence of oxygen acts as a sensitizer for photo-oxidation in the vegetation, and applying a charge of the concentration of dye to soil in the vicinity of the roots of the vegetation, thereby leading to the absorption of the charge by the roots of the vegetation such that the dye will react with proteins, fatty acids, and lipids at cellular membranes of the vegetation causing membrane lipid peroxidation, and as a result of the reaction, causing the destruction of cells and tissues therein and the subsequent death of the vegetation.

7 Claims, No Drawings

MARIJUANA ERADICATION USING FLUORESCEIN DYES

BACKGROUND OF THE INVENTION

1. Field of the Invention

This invention relates to a non-toxic method of eradicating vegetation through the application of a fluorescein or like dye to the vegetation, thereby resulting in an effective, cost efficient, quick acting, and safe means of disposing of unwanted or hazardous vegetation.

2. Description of the Prior Art

Unwanted vegetation includes vegetation that the weekend gardener characterizes as weeds; vegetation that exhibits uncontrollable growth, such as the fast growing vine kudzu which takes over telephone poles, power lines, plants, trees and anything else in its path; and unlawful vegetation, such as the marijuana, coca and poppy plants. For all of these types of vegetations, it would be highly desirous to have a cost efficient, quick acting, easy to apply, and non-toxic method of eradication.

The eradication of the marijuana plants by law enforcement officials is of particular importance and difficulty, thereby requiring a new effective eradication means. A currently and extensively used method of eradication involves manual removal of the vegetation, and has many disadvantages. This type of eradication is expensive, time consuming, and dangerous, as it requires the marijuana plants be cut down and either hauled away to often distant loading trucks outside inaccessible fields, or burned on the spot. These activities carry with them the dangers of swinging machetes, heat exhaustion and confrontations with poisonous snakes, or the need to use large quantities of flammable fuel, to burn the green marijuana plants, which can lead to brush fires and pollution. Additionally, cultivation of marijuana plants by growers is a profitable business, and many growers arm themselves heavily in order to protect their crops, using snipers and booby traps in an effort to intimidate federal employees and public land users.

Another method of eradication often used involves the use of herbicides. While non-toxic herbicides are preferable, their general ineffectiveness leads to the more frequent use of toxic herbicides. Unfortunately, these highly toxic herbicides, such as Paraquat which has been used extensively for the eradication of the marijuana plant, are undetectable by ordinary means once sprayed on the vegetation. Thus, there is nothing to prevent an unscrupulous grower from harvesting the marijuana plants and selling it to unsuspecting buyers even after it has been contaminated.

As a result of the disadvantages of these prior methods of eradicating vegetation such as the marijuana plant, an improved method is needed. Applicant's method is designed specifically to be highly effective and overcome many of the dangers involved with prior methods of eradication. Further, Applicant's method which uses a fluorescein dye, facilitates safe and easy application, provides discoloration of the harmful vegetation such that its treatment is highly noticeable, and reacts quickly.

Other uses of fluorescein dye can be seen in U.S. Pat. No. 4,781,843 which recites a process whereby the fluorescein dyes control algae growth in open water systems, such as a water cooling towers, by absorbing and accordingly blocking the light necessary for photosynthesis, and thereby preventing algae growth. This method does not utilize or suggest direct absorption through the roots of vegetation resulting in the death of grown plants.

SUMMARY OF THE INVENTION

The present invention relates to the process of preparing a predetermined concentration of fluorescein or like dye, and applying a charge of the concentration of the dye, using dispersement means, to soil in the vicinity of the roots of the vegetation for subsequent absorption thereby, so as to initiate a reaction with proteins, fatty acids, and lipids at cellular membranes of the vegetation, which causes membrane lipid peroxidation, resulting in the death of the vegetation by destruction of the cells and tissues therein.

The main object of the present invention is to provide a process of eradicating unwanted vegetation that is easy to apply and quick acting. More specifically, in the case of eradicating marijuana plants, the purpose is to remove the need for manual eradication and allow law enforcement officials to apply a charge of a predetermined concentration of dye to the marijuana plants, post signs, and walk away since the treated crops will no longer be valuable nor harvested by growers.

Another object of the present invention is to provide a process of eradicating unwanted vegetation which is environmentally conscious, and is safe to animals or humans if accidental ingestion of the treated vegetation occurs.

Yet another object of the invention is to cause unwanted vegetation to turn substantially the color red, thereby giving notice to animals and humans that the vegetation has been treated. For marijuana plants, to make the treated plant readily identifiable to law enforcement, growers, and prospective buyers.

A further object of the invention is to cause an unpleasant odor if the treated vegetation is burned. For marijuana plants, this functions as an additional means to notify a user that the plant was treated.

Various other objects and advantages of the present invention will be readily apparent from the following description.

DETAILED DESCRIPTION OF THE PREFERRED EMBODIMENT

According to the present invention, for eradicating unwanted vegetation, a predetermined concentration of dye is prepared and subsequently applied to the soil in the vicinity of the roots for absorption thereby.

Fluorescein dyes are preferred for use in the process of the invention and include D & C Red. No. 22 or D & C Red No. 28. D & C Red No. 28 is also known as Eosine Blue, Acid Red 92, Eosine Blush and Phloxine B. These dyes are photodynamic pigments that are inactive in the absence of either light or oxygen, but in the presence of oxygen, they absorb a photon of light and are raised to an excited state, whereby they become a sensitizer in the process known as photo-oxidation. The sensitizer interacts with oxygen known as singlet oxygen, which can react with a wide variety of substrates, to give a fully oxidized form of the substrate, and subsequently regenerates and is capable of absorbing an additional photon of light repeating the cycle. The dye, therefore, acts as a true catalyst in the oxidative process, such that a small amount of dye can cause a large amount of oxidative damage.

The site of action to the photodynamic dye is dependent upon what tissues the dye is capable of penetrating and to what molecules it binds. These dyes typically react with proteins, fatty acids, and lipids at cellular membranes causing membrane lipid peroxidation, resulting in death of the cells and related tissues.

For eradicating the illegal marijuana plant, the predetermined concentration of dye and charge includes a weight of 6/10 pounds of dye dissolved in a gallon of water to form a dye solution. The charge is then applied to the soil in the vicinity of the base of the stem, approximately 4 to 6 inches from the stem, at a rate of 40 milliliters of dye solution per marijuana plant. Thus one gallon will treat approximately 94 plants, and the rate results in the consistent killing of plants of up to 6 feet in height. Further, plants are dead in 24 to 48 hours after application.

The charge of dye solution may be applied to the base of the stem of marijuana plants using a handheld spraying apparatus or, on a larger scale, it may be applied using aerial spraying means. In the case of aerial spraying, a spraying apparatus could be hung from a helicopter, wherein the apparatus is specially adapted to disperse the solution at a controlled rate and volume so as to apply the solution to the base of the marijuana plants in an effective manner.

In the preferred embodiment, the dye is of such a nature that it does not stick to the leaves of the vegetation, but rather falls to the soil for absorption through the roots of the vegetation. Accordingly, dispersement may be performed from a helicopter or like elevated vantage point.

Now that the invention has been described, what is claimed is:

1. A method of eradicating marijuana plants comprising the steps of:
   preparing a predetermined concentration of a regenerative fluorescein dye, said dye being a photodynamic pigment which in the presence of oxygen acts as a sensitizer for photo-oxidation in the vegetation, and
   applying a charge of said concentration of dye, using dispersement means, to soil in the vicinity of the roots of said vegetation for subsequent absorption thereby, so as to initiate a reaction between said concentration of dye and proteins, fatty acids, and lipids at a cellular membrane of the vegetation, which thereby causes membrane lipid peroxidation, resulting in the destruction of cell fibers in said vegetation and the subsequent death thereof.

2. The method recited in claim 1 wherein said dye is D & C Red No. 28.

3. The method recited in claim 2 further comprising the step of dissolving said dye in water at approximately 6/10 pounds of said dye per gallon of said water to form a dye solution.

4. The method claimed in claim 3 wherein said charge is applied at a rate of 40 milliliters of said dye solution per said marijuana plant.

5. The method recited in claim 4 wherein said dye solution is applied to a base of a stem of said marijuana plant.

6. The method recited in claim 5 wherein said dye does not stick to leaves of said vegetation.

7. The method recited in claim 6 wherein said dispersement means includes a helicopter having a sprayer apparatus.

* * * * *